(12) United States Patent
Guckenberger

(10) Patent No.: US 11,826,800 B2
(45) Date of Patent: Nov. 28, 2023

(54) CLEANING SYSTEM

(71) Applicant: Emack Industries, LLC, Hicksville, NY (US)

(72) Inventor: Kevin M. Guckenberger, Hicksville, NY (US)

(73) Assignee: Emack Industries, LLC, Hicksville, NY (US)

(*) Notice: Subject to any disclaimer, the term of this patent is extended or adjusted under 35 U.S.C. 154(b) by 0 days.

(21) Appl. No.: 17/174,360

(22) Filed: Feb. 12, 2021

(65) Prior Publication Data

US 2021/0346920 A1  Nov. 11, 2021

Related U.S. Application Data

(63) Continuation of application No. 16/907,747, filed on Jun. 22, 2020, now Pat. No. 11,370,002.

(60) Provisional application No. 63/020,524, filed on May 5, 2020.

(51) Int. Cl.
| | | |
|---|---|---|
| B08B 9/032 | (2006.01) | |
| B08B 7/04 | (2006.01) | |
| A61B 90/70 | (2016.01) | |
| B08B 5/02 | (2006.01) | |

(52) U.S. Cl.
CPC ............ B08B 9/0328 (2013.01); A61B 90/70 (2016.02); B08B 5/02 (2013.01); B08B 7/04 (2013.01); B08B 2209/032 (2013.01)

(58) Field of Classification Search
CPC ......... A61B 1/121; A61B 1/123; A61B 1/125; A61B 90/70; B08B 5/02; B08B 9/032; B08B 9/0321; B08B 9/0327; B08B 9/0328

See application file for complete search history.

(56) References Cited

U.S. PATENT DOCUMENTS

| | | | | |
|---|---|---|---|---|
| 5,526,841 A | * | 6/1996 | Detsch ................. | A61C 1/0007 134/102.2 |
| 5,746,596 A | * | 5/1998 | Gallant ................. | A61C 3/025 433/88 |
| 6,076,554 A | * | 6/2000 | Jensen ................ | F16K 11/0853 251/285 |
| 6,177,018 B1 | * | 1/2001 | Ruppenthal ............... | A61L 2/24 210/101 |
| 2005/0002831 A1 | * | 1/2005 | Ashe ..................... | F16K 11/085 422/106 |
| 2014/0301871 A1 | * | 10/2014 | Rogers, Jr. ............ | A61M 16/10 417/253 |

(Continued)

FOREIGN PATENT DOCUMENTS

KR  1020060019890  * 3/2006

OTHER PUBLICATIONS

English machine translation of KR1020060019890.*

Primary Examiner — Spencer E. Bell
(74) Attorney, Agent, or Firm — Collard & Roe, P.C.

(57) ABSTRACT

A cleaning system and process for cleaning a medical system comprising at least one air source at least one cleaning solution source at least one rinsing solution source and at least one switch for switching between the at least one air source, the at least one cleaning solution source, and said at least one rinsing solution source. The process is configured to selectively provide the cleaning solution from the cleaning solution source, selectively provide the rinsing solution source, and selectively providing the air pressure to purge the lines of a medical/dental system.

18 Claims, 4 Drawing Sheets

(56) References Cited

U.S. PATENT DOCUMENTS

| | | | |
|---|---|---|---|
| 2017/0173228 A1* | 6/2017 | Ehlert | B08B 9/00 |
| 2019/0076567 A1* | 3/2019 | Yang | A61L 2/0088 |
| 2019/0134682 A1 | 5/2019 | Overmyer | |
| 2020/0271382 A1* | 8/2020 | Radford | A61B 1/125 |
| 2021/0204797 A1* | 7/2021 | Hernandez | G02B 27/0006 |

* cited by examiner

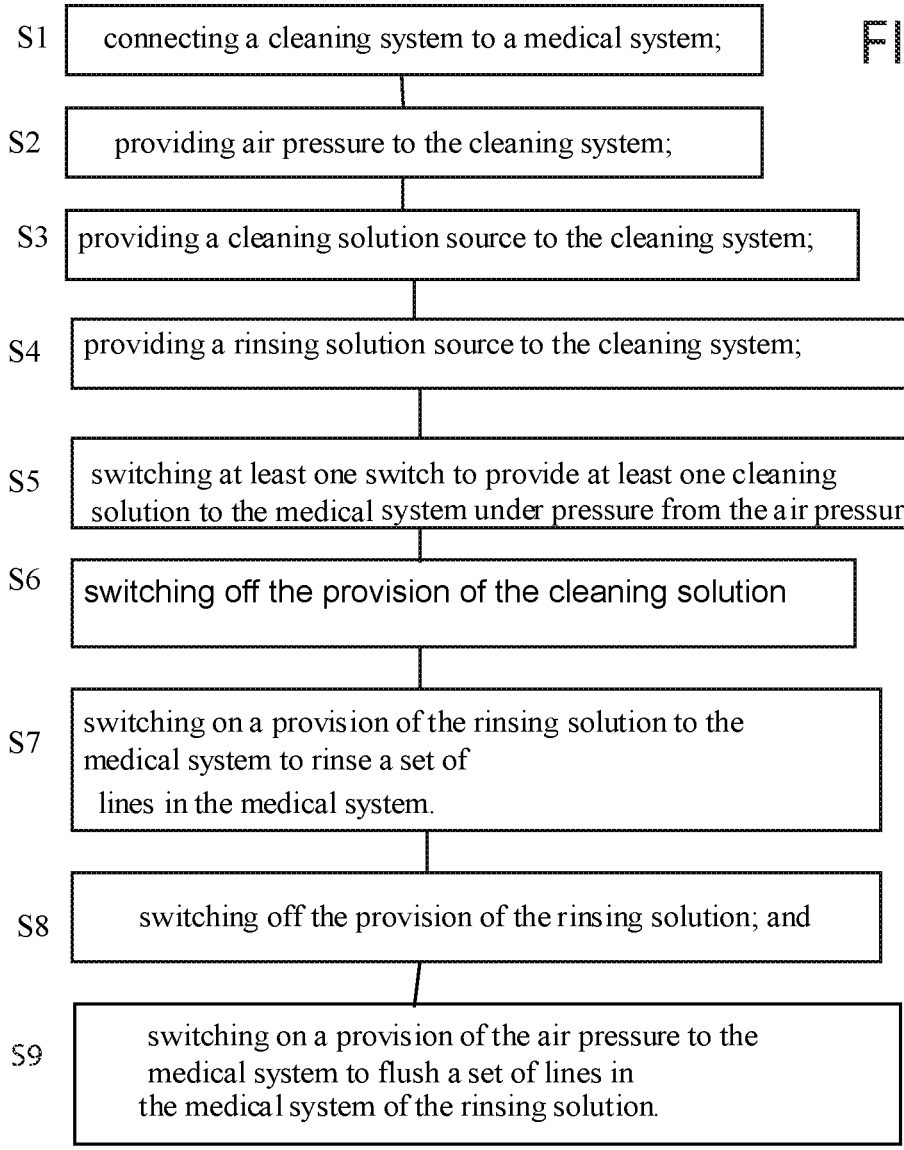

CLEANING SYSTEM

CROSS REFERENCES TO RELATED APPLICATIONS

This application is a continuation of U.S. patent application Ser. No. 16/907,747 filed on Jun. 22, 2020. The '747 application claims the benefit of provisional application Ser. No. 63/020,524 filed on May 5, 2020. This application is also a non-provisional a application claiming the benefit of provisional application Ser. No. 63/020,524 filed on May 5, 2020, the disclosures of all of these applications hereby incorporated herein by reference in their entirety.

BACKGROUND OF THE INVENTION

One embodiment of the invention relates to a cleaning system such as a dental cleaning system which is configured to be used for cleaning the lines of a dental office. This dental cleaning system can be used to essentially wash the inner lines of a dental service station.

Medical or dental systems which are first put into operation or which have laid dormant for an extended period of time can have a build up of biological material inside of the lines of the medical or dental system. The build up of biological material can be harmful for patients who are flushing their mouths with water that includes this biological material, it is beneficial to have the lines periodically flushed out via a cleaning system which is configured to efficiently clean these lines in a safe manner.

SUMMARY OF THE INVENTION

A cleaning system and process for cleaning a medical system comprising at least one air source at least one cleaning solution source at least one rinsing solution source and at least one switch for switching between the at least one air source, the at least one cleaning solution source, and said at least one rinsing solution source. The process is configured to selectively provide the cleaning solution from the cleaning solution source, selectively provide the rinsing solution source, and selectively providing the air pressure to a medical system.

A process for cleaning a medical system using a cleaning system comprising at least one air source, at least one cleaning solution source, at least one rinsing solution source, and at least one switch for switching between the at least one air source, the at least one cleaning solution source, and said at least one rinsing solution source.

The process comprises of connecting the cleaning system to the medical system so as to provide air pressure to the cleaning system. In another step the process includes providing a cleaning solution from cleaning solution source to the cleaning system. Another step involves providing a rinsing solution from said rinsing solution source to the cleaning system. One other step includes switching at least one switch to provide at least one cleaning solution, at least one rinsing solution or air pressure to the medical system.

BRIEF DESCRIPTION OF THE DRAWINGS

These and other benefits and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 4 is a process for cleaning a medical system.

DETAILED DESCRIPTION OF THE PREFERRED EMBODIMENTS

Figure 1:
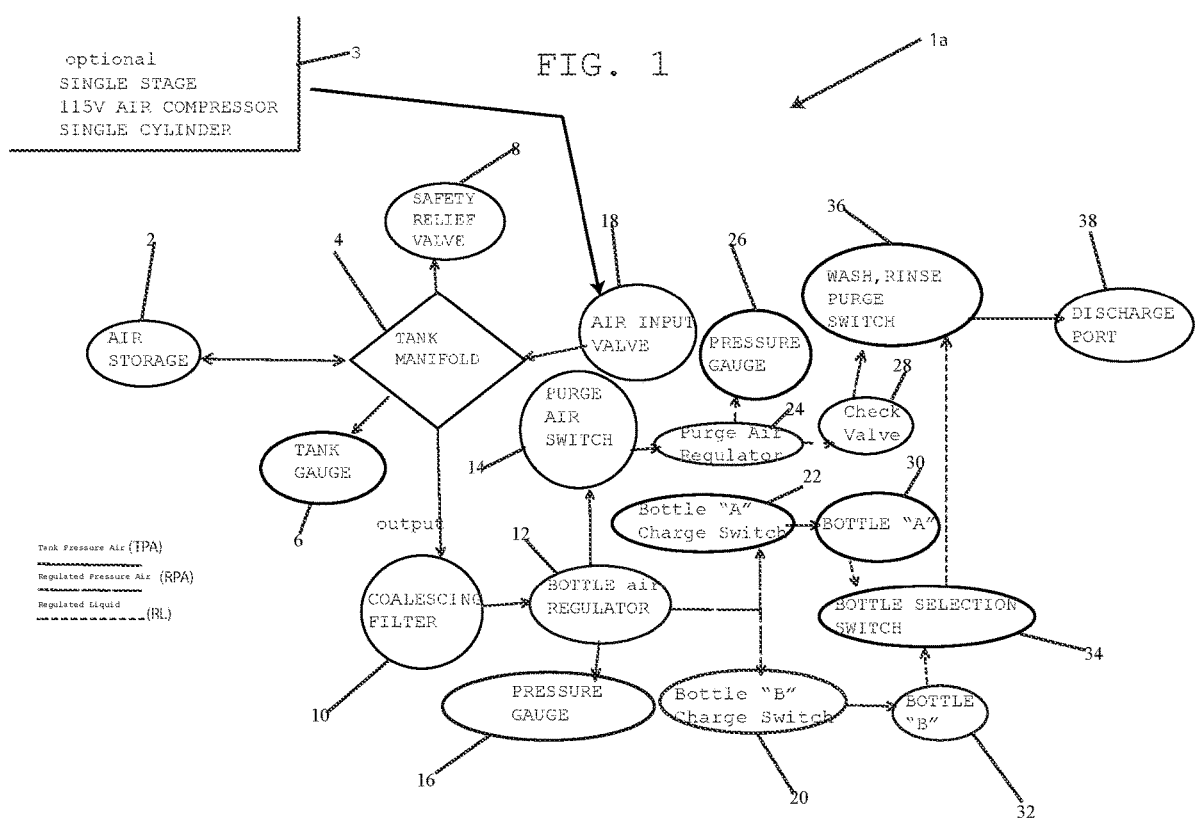
FIG. 1. shows a first block diagram of a first embodiment of the invention.

Referring now in detail to the drawings and, in particular, FIG. 1 shows a block diagram of a first embodiment 1*a* which includes an air pressure storage tank 2 While the storage tank can be of any suitable type, in at least one embodiment the tank is an aluminum 7 gallon tank. There is also an optional single stage air compressor 3 which is configured to provide air to the air storage 2. An output of air storage 2 is configured to connect to an input of tank manifold 4 which in at least one embodiment is at least a partially brass or similar type manifold which is configured to receive a plurality of different lines. Coupled to tank manifold 4 is a tank gauge 6 which reads the pressure in the tank manifold. There is also a safety relief valve 8 which is configured to relieve pressure in the system when air is of a pressure that is higher than a predetermined pressure. The aft from single stage air compressor 3 and or air from the system located in the doctor's and/or dentist's office is configured to be input into the system via air input valve 18. Air flowing out from the manifold 4 is configured to flow through coalescing filter 10.

Air from coalescing filter 10 flows into bottle air regulator 12. Bottle air regulator 12 is configured to regulate the air pressure from the air storage 2 as well as provide regulated pressure to downstream bottles of either cleaning solution stored in a first bottle 30, or a rinsing solution in bottle 32. Bottle air regulator 12 has an output coupled to pressure gauge 16 and another output coupled to purge air switch 14 which is configured to selectively allow purging air pressure to flow through the tubes of the medical system. This purge air switch 14 is a toggle switch which allows the user to manually purge air through the system. As described above, the bottle air regulator 12 has its output which is fed into a charge switch 22 for the first bottle 30 containing the cleaning solution. In addition, air regulator 12 has its output which is fed into a charge switch 20 which has its output which feeds into a second bottle 32 which houses the rinse.

In at least one embodiment the cleaning solution comprises a bleach solution. In another embodiment, the cleaning solution comprises a bleach and further agent composite. In one embodiment the rinsing solution comprises water.

The output of the first bottle 30 containing the cleaning solution is fed into bottle selection switch 34. In addition, the second bottle 32 has its output which feeds into the bottle selection switch 34. The bottle selection switch 34 is configured to selectively allow fluid to flow into the wash, rinse and purge switch 36. The output of the wash, rinse and purge switch is fed into the discharge port 38. The discharge port is coupled to the medical or dental device which is then flushed with either the cleaning solution (such as a bleach solution), the rinsing solution (such as water) or air.

While pressure can be fed into the bottles 30 and 32 pressurizing the fluid in these bottles, the pressure such as air pressure can be fed as air from the purge air switch 14 into the purge air regulator 24. From the purge air regulator, the air flows into pressure gauge 26 to provide a reading of air pressure in the soon to be discharged air. The output of the purge air regulator 24 flows into the input of the check valve 28. The check valve 28 is configured as a backflow check valve which prevents fluid such as cleaning fluid or rinsing fluid to flow back into the air lines. Air flowing from the check valve 28 flows into the wash, rinse, and purge switch such that a user can then selectively elect to discharge pressurized air from the system to completely flush the lines of the medical and/or dental system with air.

While the lines in the cleaning system and in the medical and/or dental system can be of any type or shape, in at least one embodiment, the lines of this system are configured as ¼ inch poly tubing.

Figure 2:
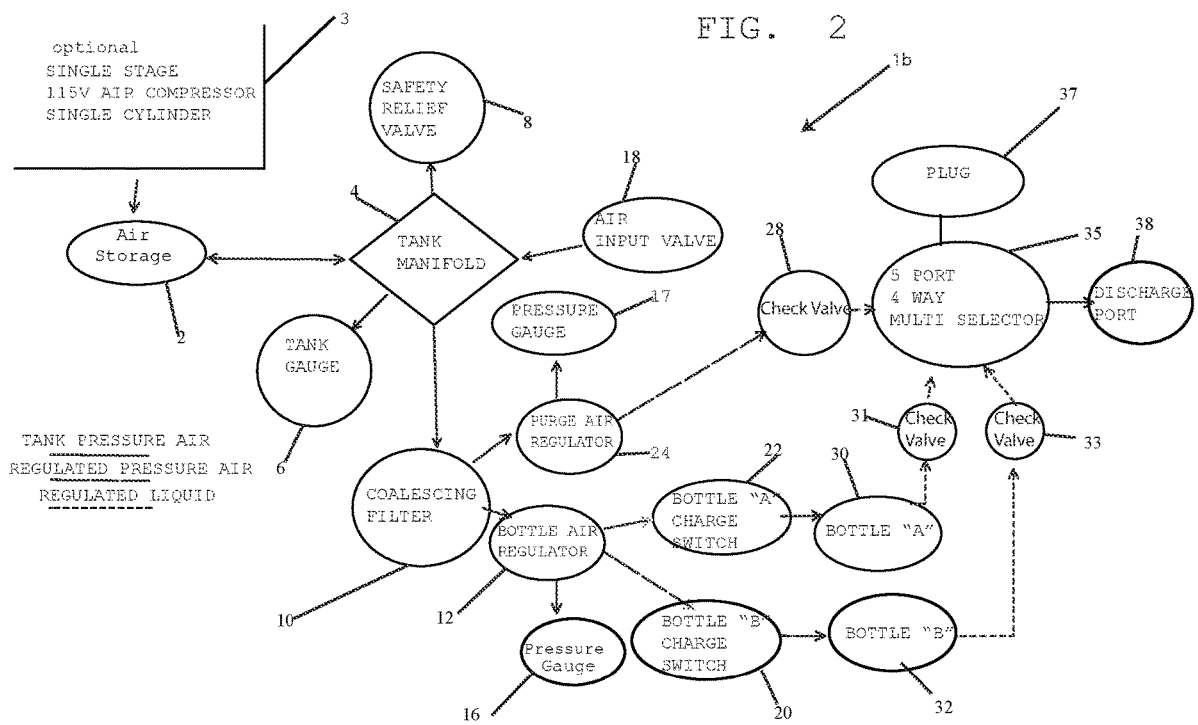
FIG. 2 shows a second block diagram of a second embodiment of the invention.

FIG. 2 is another embodiment of the invention 1b wherein in this view there are similar components to that shown in FIG. 1. All of the components numbered the same are the same components in purpose and function. However, in this view coalescing filter 10 has connected to it both bottle air regulator 12 as well as a purge air regulator 24. This purge air regulator is coupled directly to coalescing filter 10 so that the presences of the five (5) port four (4) way multi selector 35 can take the place of at least the purge air switch 14. The five port 4-way multi selector switch 35 also takes the place of the bottle selection switch 34, as well as the wash, rinse and purge switch 36. In the case of the five (5) port four (4) way multi selector switch 35, a plurality of check valves 28, 31 and 33 are configured to connect this device to the different feeds. These check valves 28, 31 and 33 are configured as one-way check valves which are configured to keep any fluid from flowing into the air lines or to keep any air from flowing back into the fluid lines as well. For example, check valve 28 is positioned between selector 35 and purge air regulator 24. Check valve 31 is positioned between bottle "A" having the cleaning solution and the selector 35. Check valve 33 is positioned between bottle "B" and selector 35. In addition, coupled to selector 35 is a plug 37 which is coupled to at least one output, and a discharge port 38 coupled to another port of the selector 35.

The output of the discharge port can be any one of the cleaning solution from bottle "A" 30 or the rinsing solution from bottle "B" 32, or air from the purge air regulator 24.

Figure 3:
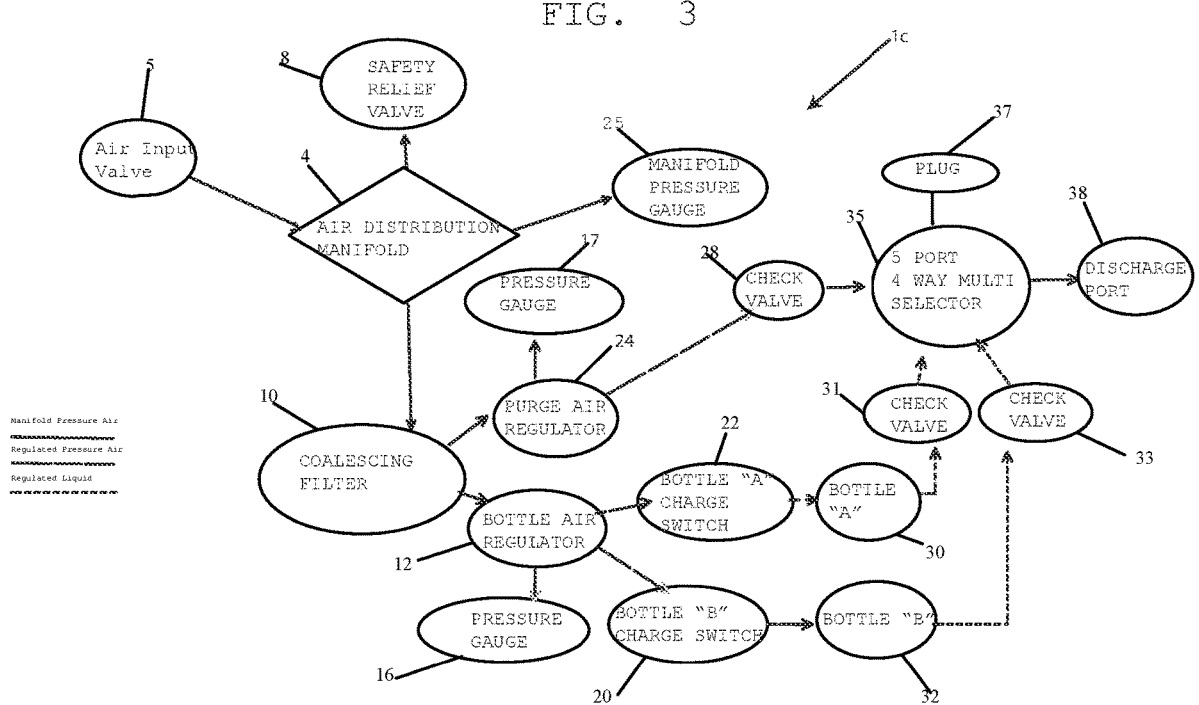
FIG. 3 shows a third block diagram of the third embodiment of the invention.

FIG. 3 is another embodiment of the invention 1c which is configured to not have either an air storage tank 2 or an input from an optional single stage air compressor. Instead all air pressure is fed from a connection by the air input valve 5. Thus, there is no need for the air tank 2 or the additional compressor 3. Thus, this design is a simplified design which makes for a more compact, office staff usable, portable design.

FIG. 4 is a flow chart for the process for cleaning a medical system such as a dental system. The process starts in step S1 wherein a user connects a cleaning system to a medical system. Next, in step S2, the user provides air pressure to the cleaning system by connecting air to the system either by connecting an air storage tank such as air storage tank 2 to a tank manifold such as tank manifold 4. Alternatively, an in-house air pressure system can be connected to the tank manifold 4 via air input valve 18. Next, in step S3, the user can provide a cleaning solution source to the cleaning system. The cleaning solution source can be in the form of a cleaning solution which is stored in a storage unit such as bottle "A" 30 which is coupled to discharge port 38. This cleaning solution is provided under pressure such as under air pressure wherein this air pressure flows through bottle air regulator 12 to provide air pressure to both bottle "A" and to bottle "B" 32. As discussed above a switch 22 is configured to selectively provide air pressure to bottle "A" 30.

Step 34 includes providing a rinsing solution through the rinsing solution source such as bottle "B" 32 to the cleaning system. Thus, a user can selectively activate switch 20 to provide pressure to release the rinsing solution to flow through the cleaning system and into the medical system to rinse the lines of the medical system after the cleaning solution has passed through the lines of the medical system.

In at least one embodiment, in step 35 the cleaning solution can be infected into the medical system wherein the cleaning solution can then sit inside the lines of the medical system and treat the biological residue inside of the lines. In at least one embodiment the cleaning solution is made from a bleach or chlorine-based solution. In another embodiment the cleaning solution can be made from a bleach and another activating agent. While bleach can be used other components for cleaning can also be used for the cleaning solution.

Once the cleaning solution has settled inside of the lines of the medical system for a predetermined period of time, a user can then shut off the provision of the cleaning solution in step S6. Next, in step S7 these lines can be rinsed. Thus, a user can then selectively switch on the provision of the rinsing solution to the medical system to rinse the set of lines inside of the medical system.

Next, in step S8 the user can switch off the provision of the rinsing solution. Next, in step S9, the user can then switch on the provision of the air to completely flush out and dry the inside of the lines and leave the system clean, dry and ready to use.

Thus, there is provided both a system and process to clean a medical system such as a dental cleaning system which has water-based lines which may have become compromised with biological material through inaction. This system can then thoroughly clean these lines in an economical manner.

Accordingly, while several embodiments of the present invention have been shown and described, it is obvious that many changes and modifications may be made thereunto without departing from the spirit and scope of the invention.

What is claimed is:

1. A portable cleaning system for cleaning a medical system comprising:
   one air source;
   at least one cleaning solution source;
   at least one rinsing solution source;
   at least one bottle air regulator configured to provide regulated air pressure to both said cleaning solution source and said at least one rinsing solution source;
   wherein said bottle air regulator is downstream from said air source and is configured to receive pressurized air from said air source;
   at least one five port four way multi selector switch coupled to each of the air source, the cleaning solution source and the rinsing solution source, the five port four way multi selector switch for switching between the at least one air source, the at least one cleaning solution source, and said at least one rinsing solution source;
   at least one discharge line having at least one discharge port coupled to the at least one five port four-way multi selector switch;
   at least one bottle charge switch positioned upstream of at least one of said cleaning solution source and said rinsing solution source to selectively allow pressurization of at least one of said cleaning solution source and said rinsing solution source;

at least one plug coupled to an output of the five port four way multi selector switch; and wherein the air source provides pressure to the cleaning solution and the rinsing solution upstream of the five port four-way switch;

wherein said at least one discharge port is configured to feed into a medical system and wherein the five port-four way switch is configured to accept a feed from said at least one air source, said at least one cleaning solution source, and said at least one rinsing solution source, to selectively feed either a cleaning solution, a rinsing solution, or pressurized air from said air source into said discharge line or to close input into said discharge line via said plug and such that when the five port-four way switch is turned to the plug, the plug stops flow into said discharge line;

wherein said at least one bottle charge switch positioned upstream of at least one of said cleaning solution source and said rinsing solution source comprises two separate bottle charge switches with a first bottle charge switch to selectively allow pressurization of said cleaning solution source and a second bottle charge switch to selectively charge said rinsing solution source and wherein said at least one bottle charge switch is configured to remove pressure from the rinsing solution source so that the rinsing solution source can be replaced while the cleaning system is in operation with the lines charged with pressure.

2. The cleaning system as in claim 1, further comprising at least one check valve positioned between said at least one switch and said at least one air source.

3. The cleaning system as in claim 1, further comprising at least one check valve positioned between said at least one switch and said at least one cleaning solution source.

4. The cleaning system as in claim 1, further comprising at least one check valve positioned between said at least one switch and said at least one rinsing solution source.

5. The cleaning system as in claim 1, wherein said at least one air source further comprises at least one coalescing filter.

6. The cleaning system as in claim 1, wherein said at least one air source further comprises at least one manifold for receiving air from an air input.

7. The cleaning system as in claim 6, further comprising at least one safety relief valve coupled to said at least one manifold.

8. The cleaning system as in claim 6, further comprising at least one manifold pressure gauge configured to provide at least one reading of the pressure inside of the manifold.

9. The cleaning system as in claim 1, further comprising at least one pressure gauge coupled to said at least one bottle air regulator.

10. The cleaning system as in claim 1, wherein said cleaning solution source comprises a bottle of cleaning solution.

11. The cleaning system as in claim 1, wherein said rinsing solution source comprises a bottle of water.

12. The cleaning system as in claim 1, further comprising a plurality of pneumatic lines, wherein said at least one air source, at least one cleaning solution source; at least one rinsing solution source; and said at least one switch are each coupled together via at least one of said plurality of pneumatic lines.

13. The cleaning system as in claim 1, further comprising at least one check valve coupled to said five port four-way switch.

14. The cleaning system as in claim 1, further comprising at least one purge air regulator configured to provide air pressure to said at least one five port four way multi selector switch separate from said at least one bottle air regulator.

15. The portable cleaning system as in claim 1, wherein the cleaning system comprises at least three separate charged lines with a first line comprising an air regulator and a check valve in series, a second line comprising a regulator, a charge switch, a rinsing bottle, and a check valve in series, and a third line comprising a regulator, a charge switch, a cleaning solution bottle, and a check valve in series with each line feeding into said five port four way multi selector switch.

16. The portable cleaning system as in claim 15, wherein said bottle air regulator comprises four ports, with a first port being an input port to receive pressurized air from said air source, a second port coupled to a pressure gauge, a third port coupled to said second line, and a fourth port coupled to said third line.

17. The portable cleaning system as in claim 16, wherein said five port four way multi selector switch is configured to be manually operable by a single operator to selectively switch between an input from at least one of said first line, said second line and said third line and to selectively output an output from at least one of said first line, said second line, and said third line into said discharge port.

18. A portable cleaning system for cleaning a medical system comprising:

one air source;

at least one cleaning solution source;

at least one rinsing solution source;

at least one coalescing filter coupled to said at least one air source;

at least one bottle air regulator configured to provide regulated air pressure to both said cleaning solution source and said at least one rinsing solution source;

at least one purge air regulator;

wherein said coalescing filter has an output that feeds into said at least one purge air regulator and into said bottle air regulator and wherein said coalescing filter is configured to provided pressurized air to said at least one bottle air regulator and said at least one purge air regulator;

at least one five port four way multi selector switch coupled to each of the air source, the cleaning solution source and the rinsing solution source, the five port four way multi selector switch configured to receive pressurized air, pressurized cleaning solution and pressurized rinsing solution and configured for switching between the at least one air source, the at least one cleaning solution source, and said at least one rinsing solution source;

wherein the air source provides pressure to the cleaning solution and the rinsing solution upstream of the five port four-way switch;

at least one discharge line having a discharge port coupled to the at least one five port four way multi selector switch;

at least one plug coupled to an output of the-five port four way multi selector switch;

at least one bottle charge switch positioned upstream of at least one of said cleaning solution source and said rinsing solution source to selectively allow pressurization of at least one of said cleaning solution source and said rinsing solution source;

wherein said at least one five port four way multi selector switch has at least three separate inputs and one output feeding into said at least one discharge line;

wherein the system is configured as portable and compact and wherein once the system is coupled to an air source and to a medical system, the system is configured to clean, rinse, and purge lines of the medical system without disconnecting the system from the air source, and wherein the five port-four way switch is configured to accept a feed from said at least one air source, said at least one cleaning solution source, and said at least one rinsing solution source, to selectively feed either a cleaning solution, a rinsing solution, or pressurized air from said air source into said discharge line or to close input into said discharge line via said plug and such that when the five port-four way switch is turned to the plug, the plug stops flow into said discharge line;

wherein said at least one bottle charge switch positioned upstream of at least one of said cleaning solution source and said rinsing solution source comprises two separate bottle charge switches with a first bottle charge switch to selectively allow pressurization of said cleaning solution source and a second bottle charge switch to selectively charge said rinsing solution source and wherein said at least one bottle charge switch is configured to remove pressure from the cleaning solution source so that the cleaning solution source can be replaced while the cleaning system is in operation with the lines charged with pressure.

* * * * *